United States Patent [19]

Pacey et al.

[11] 4,436,923
[45] Mar. 13, 1984

[54] TRIFLUOROMETHYL-SUBSTITUTED CHROMOGENIC CROWN ETHERS AND METHODS OF USING SAME

[75] Inventors: Gilbert E. Pacey; Benard P. Bubnis, both of Oxford, Ohio

[73] Assignee: The President and Trustees of the Miami University, Oxford, Ohio

[21] Appl. No.: 386,066

[22] Filed: Jun. 7, 1982

[51] Int. Cl.$^3$ ............................................ C07D 323/00
[52] U.S. Cl. ....................................... 549/352; 436/74; 436/79
[58] Field of Search ........................................ 549/352

[56] References Cited

PUBLICATIONS

Chem. Abstracts 95: 107924t.
G. E. Pacey & B. P. Bubnis, A New Chromogenic Crown Ether 4″-Cyano-2″,6″-Dinitro-4′-Aminobenzo-15-Crown-5 as an Alkali Metal Extraction Reagent, *Analytical Letters*, 13(A12), 1085-1091 (1980).
Nakamura, H., Takagi, M., Ueno, K., Complexation and Extraction of Alkali Metals Ions by 4′-Picrylaminobenzo-18-Crown-6 Derivatives, *Anal. Chem.*, 1980, 52, 1668.
Nakamura, H., Takagi, M., Ueno K. Photometric Reagents and Alkali Metal Ions, Based on Crown-Ether Complex Formation-III, 4′-Picrylaminobenzo-15-Crown-5 Derivatives, *Talanta*, 1978, 26, 921.
Takagi, M., Nakamura, H., Ueno, K., A Novel Colorimetric Reagent for Potassium Based on Crown Ether Complex Formation, *Anal. Lett.*, 1977, 10, 1115.

Primary Examiner—Ethel G. Love
Attorney, Agent, or Firm—Merriam, Marshall & Bicknell

[57] ABSTRACT

Two novel trifluoromethyl-substituted chromogenic crown ethers are disclosed, 4′-(2″,6″-dinitro-4″ trifluoromethylphenyl) aminobenzo-15-crown-5 and 4′-(2″,4″-dinitro-6″-trifluoromethylphenyl) aminobenzo-15-crown-5. These compounds are useful as reagents for the extraction and spectrophotometric determination of potassium in the presence of sodium. The compounds, their methods of manufacture, and methods of utilizing the compounds for the analysis of potassium are disclosed and claimed.

4 Claims, 3 Drawing Figures

TRIFLUOROMETHYL-SUBSTITUTED CHROMOGENIC CROWN ETHERS AND METHODS OF USING SAME

BACKGROUND OF THE INVENTION

The present invention relates to certain chromogenic crown ethers and to the use of these ethers as reagents for the extraction and spectrophotometric determination of potassium. The new reagent compounds have the structural formula:

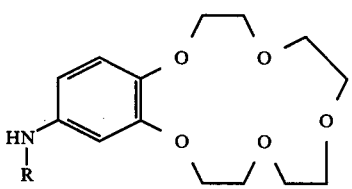

where R is taken from the group consisting of

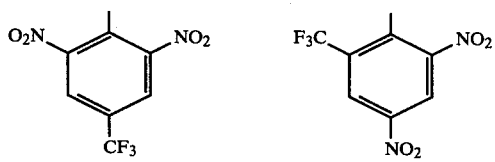

These crown ethers are systematically named 4'-(2'',4''-dinitro-6''-trifluoromethyl-phenyl) aminobenzo-15-crown-5 and 4'-(2'',6''-dinitro-4''-trifluoromethylphenyl) aminobenzo-15-crown-5, respectively.

Selective reagents which permit the isolation of a particular ion or ions from a complex matrix are of economic interest. In particular, with respect to the potassium and sodium ions which are present in many biological systems, a reagent having the ability to selectively (and quantitatively) extract one of these ions in the presence of the other would be of interest in biochemical assays.

The ability of crown ethers to selectively extract alkali and alkaline earth metal ions has been recognized in the art [Pedersen, C. J., *J.Am.Chem.Soc.*, 1967, 89, 7017]. Nonetheless, there has been little successful work in utilizing these compounds in analytical determinations until quite recently.

Of particular interest to the background of the present invention, is the description of the synthesis of a chromogenic crown-like compound, 4'-picrylaminobenzo-15-crown-5, which was reported to be a selective extractant for potassium ions (10–800 p.p.m.) in the presence of sodium ions (2300 p.p.m.) [Takagi, M., Nakamura, H., and Ueno, K., *Anal. Lett.*, 1977, 10, 1115]. Unlike the case with the reagents of the present invention, however, the 4'-picrylaminobenzo-15-crown-5 reagent suffers both from a poor extraction efficiency and from spectral overlap of its protonated (HL) and deprotenated (ML) species. That is to say, the reagent can be used to extract K+ from solution by forming a complex of the form.

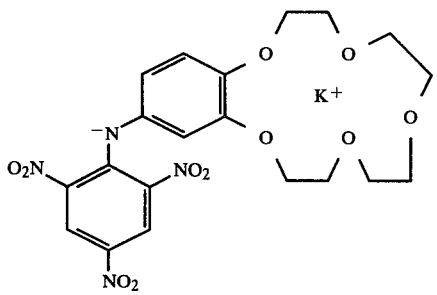

This (ML) compound, however, has a considerable spectral overlap with the unreacted reagent precursor (HL) compound Moreover, this picryl crown ether reagent does not readily quantitively extract K+ in the presence of Na+. These same workers have reported efforts to improve the extraction efficiency of these reagent materials by adding bromo and nitro groups in the 5' position [Nakamura, H., et al., *Talanta*, 1978, 26, 921; Nakamura, H., et al., *Anal. Chem.*, 1980, 52, 1668].

SUMMARY

The present invention provides novel chromogenic crown ethers which function as analytical reagents for potassium. Both species of the novel reagent exhibit good extraction efficiencies and large differences in the value of the λ max and molar absorptivity between the complexed (ML) and uncomplexed (HL) species.

Both compounds are resistant to the influence of sodium ion on the determination. Experimental data indicates a linear range of 5 to 700 p.p.m. in the presence of as much as 3000 p.p.m. of sodium ion. The reagents are sensitive to rubiduim ion at a concentration of 1000 p.p.m. As rubiduim has a low natural occurence, this should not be a problem in real samples.

BRIEF DESCRIPTION OF THE DRAWINGS

FIG. I is the ultraviolet-visible spectra of protonated (HL) and deprotonated (ML) crown ethers: (a) 4'-picrylaminobenzo-15-crown-5, $2\times10^{-4}$M in 10% dioxan-water; (b) 4'-(2'',4''-dinitro-6''-trifluoromethylphenyl) aminobenzo-15-crown-5, $2\times10^{-4}$M in 40% acetonitrile-water; and (c) 4'-(2'',6'' dinitro-4''-trifluoromethyl) aminobenzo-15-crown-5, $2\times10^{-4}$M in 40% acetonitrile-water.

DESCRIPTION OF THE INVENTION

The compounds of the present invention are dinitro-trifluoromethylphenyl-aminobenzo-15-crown-5 ethers, viz, 4'-(2'',6''-dinitro-4''-trifluoromethylphenyl) aminobenzo-15-crown-5 (4TF) and 4'-(2'',4''-dinitro-6''-trifluoromethylphenyl) aminobenzo-15-crown-5 (6TF).

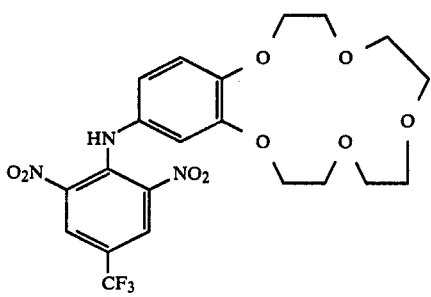

4TF

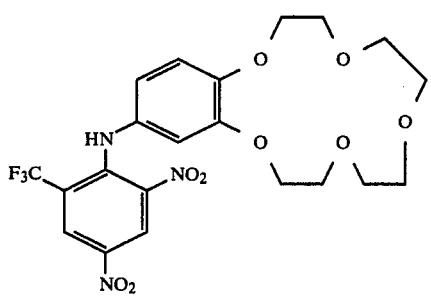

6TF

Figure 1:
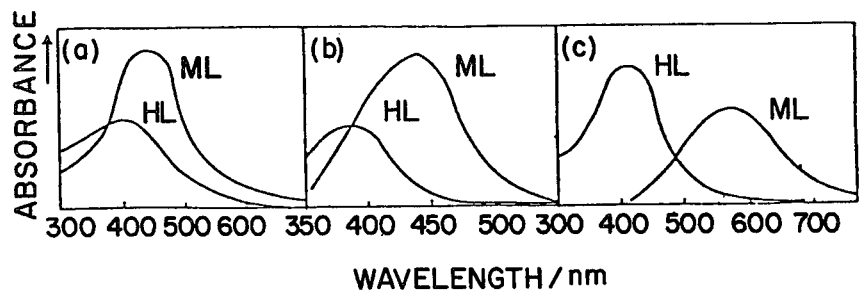

The aqueous spectra of 4TF, 6TF, and for reference purposes, 4′-picrylaminobenzo-15-crown-5, in their protonated (uncomplexed) forms (HL) and in their dissociated (complexed) forms (ML) are shown in FIG. 1. The maximum absorptions and the molar absorptivities for the reagent species of FIG. 1 are shown in Table 1.

TABLE 1

WAVELENGTH MAXIMA AND MOLAR ABSORPTIVITIES FOR CHROMOGENIC CROWN ETHERS

| Reagent | Species | $\epsilon H_2O/$ 1 mol$^{-1}$ cm$^{-1}$ | $\lambda$max.H$_2$O /nm | $\Delta\lambda$max./nm |
|---|---|---|---|---|
| 4′-Picrylamino- | HL | 13000 | 390 | 55 |
| benzyl-15- crown-5 | ML* | 20000 | 445 | |
| 4TF | HL | 6400 | 425 | 150 |
| | ML* | 4400 | 585 | |
| 6TF | HL | 13250 | 380 | 80 |
| | ML* | 20800 | 460 | |

*Depending on the alkali metal cation complexed in the crown cavity, the complexed form may be either ML or ML.HL.

A significant feature is the decrease in spectral overlap between the HL and ML species for both 4TF and 6TF. In contrast, the overlap between the HL and ML species with 4′-picrylaminobenzyl-15-crown-5 is so great that the ML species had to be determined at a wavelength where, according to molar absorptivities, considerably less than maximum absorption occurs (20,000 versus 5000 1 mol cm$^{-1}$).

Of the two compounds, 6TF is superior in terms of extraction efficiency and is capable of extracting 5 to 700 p.p.m. of potassium ions in the presence of 3000 p.p.m. of sodium ions. The 4TF compound, although somewhat inferior to the 6TF reagent in both spectral properties and extraction efficiencies, is clearly superior to the tested prior art compound.

Both 4TF and 6TF may be prepared by reacting 4′-aminobenzo-15-crown-5 with either 1-chloro-2,6-dinitro-4-trifluoromethylbenzene or 1-chloro-4,6-dinitro-2-trifluoromethylbenzene in organic solvent in the presence of a base, eg, sodium bicarbonate. The resultant products (yields 60%) comprise dark orange powders, having melting points of 171° C. (4TF) and 165° C. (6TF).

Both the 4TF and 6TF crown ethers are soluble in a variety of organic solvents. Because of the proposed use of the compounds as reagents for spectrophotometric determinations, the preferred solvent is chloroform. Of the materials tested, chloroform alone works sufficiently well, in terms of the acid-base character of the crown ether, to be used in analytical determinations. Both toluene and dichloromethane were unsatisfactory because their background blanks were too large, owing to the complicated equilibrium established between the aqueous and non-aqueous acid-base chemistry of the chromogenic crown ether.

The potassium ion analyses are preferably preformed by dissolving the crown ether in a solvent prepared by dissolving 1 mole of triethylamine in 1 liter of chloroform. Other basic compounds, soluble in both organic solvents and water and disassociating to yield a pH of >10.0 could also be used. Although the concentration of the crown ether may vary it is preferred to employ reagent solutions in the range $1\times10^{-4}$ to $1\times10^{-2}$ molar, most preferably $2\times10^{-3}$ molar.

The extractions are performed by mixing an aqueous phase containing the dissolved cation with the organic reagent solution. In view of the fact that the two phases are immiscible, it is desirable to shake or otherwise agitate the two-phase mixture to ensure that the extraction proceeds. For the same reason, it is preferred to use approximately equal volumes of organic and aqueous solutions. It was found that 5 minutes of agitation resulted in the extraction of approximately 80% of material with good precision. Therefore the results reported herein are based on a 5-minute extraction time. Other time constants could also be used.

The pH of the system was found to be critical as the amine proton on the 6TF and 4TF crown ether must dissociate in the aqueous phase before complexation and remain dissociated during and after the phase transfer. For these extractions, the pH of the aqueous phase after extraction had to be greater than 10.0 (and preferably 11), but, as a high concentration of TEA was present in the organic phase, this was easily accomplished.

After extraction, the organic and aqueous phases are permitted to separate, and the aqueous phase discarded. The organic phase containing entrapped potassium ion may be analyzed directly by spectrophotometric means. If the preferred concentration level of reagent solution is employed, however ($2\times10^{-3}$), it is generally desirable to further dilute the sample with CHCl$_3$/TEA(1M) prior to analysis as an aid to spectral resolution. A dilution of 1 ml→10 ml is preferred ($2\times10^{-4}$M, based on the original (HF) ether).

Spectrophotometric measurements were carried out using a Hewlett-Packard 8450A reversed optics spectrophotometer with 10-mm glass cells. The pH measurements were carried out using a Corning, Model 12, pH meter. Characterization of the new organic compounds was accomplished using a JEOL nuclear magnetic resonance spectrometer and a Perkin-Elmer 180 infrared spectrophotometer. All elemental analyses were performed externally by Galbraith Laboratory.

EXAMPLE I

Synthesis of 4'-(2",6"-dinitro-4"-trifluoromethylphenyl) aminobenzo-15-crown-5

4'-nitrobenzo-15-crown-5 was prepared by nitrating benzo-15-crown-5 in accordance with the procedure of Ungaro et al. [Ungaro, R., El Hag, R., and Smid, J., *J.Am. Chem. Soc.*, 1976, 98, 5198]. The nitro group was catalytically reduced with hydrogen at 30 psi in freshly distilled DMF in the presence of 10% Pd/C, forming 4'-aminobenzo-15-crown-5.

A mixture of the aminobenzo compound (3.9 g; 0.0137 mol), 1-chloro-2,6-dinitro-4-trifluoromethylbenzene (3.7 g; 0.0137 mol) and sodium bicarbonate (1.15 g; 0.0137 mol) was refluxed for 5 hours in 200 ml of absolute methanol. The mixture was cooled and filtered and the methanol was removed using a rotary evaporator. The residue was dissolved in isopropanol, and an equal volume of light petroleum (boiling range 30°–60° C.) was added in order to precipitate the impurities. The isopropanol-light petroleum mixed solvent was filtered and evaporated to give the chromogenic crown ether 4TF as a dark orange powder (melting point 171° C., yield 60%). Calculated for $C_{20}H_{22}N_3O_9F_3$: C, 48.74; H, 4.92; N, 8.12; and F, 11.02%. Found: C, 48.51; H, 4.41; N, 7.93; and F, 11.06%.

EXAMPLE II

Synthesis of 4'-(2",4"-dinitro-6"-trifluoromethylphenyl) aminobenzo-15-crown-5

4'aminobenzo-15-crown-5 was prepared in accordance with the procedure of Example I. A mixture of the aminobenzo compound (3.9 g.; 0.0137 mol), 1-chloro-2,4-dinitro-6-trifluoromethylbenzene (3.7 g; 0.0137 mol) and sodium bicarbonate (1.15 g; 0.0137 mol) was refluxed for 5 hours in 200 ml of absolute methanol. The mixture was cooled and filtered, and the methanol was removed using a rotary evaporator. The residue was dissolved in isopropanol, and an equal volume of light petroleum (boiling range 30°–60° C.) was added in order to precipitate the impurities. The isopropanol-light petroleum mixed solvent was filtered and evaporated to give the chromogenic crown ether 6TF as a dark orange powder (melting point 165° C.), yield 60%). Calculated for $C_{20}H_{22}N_3O_9F_3$: C, 48.74; H, 4.92; N, 8.12; and F, 11.02%. Found: C, 48.67; H, 4.36; N, 7.86; and F, 10.74%.

EXAMPLE III

Standarization of extraction system

Standard solutions ranging between 50 and 500 p.p.m. $K^+$ were prepared by dissolving KCl (99.9% purity) in deionized water. Five milliliter samples of each of the solutions were extracted with 5 ml solutions of 6TF reagent [$2 \times 10^{-3}$M in $CHCl_3$/TEA(1M)] by adding the organic and aqueous solutions to a test tube and shaking for five minutes. After settling, the aqueous phase was discarded, a 1 ml aliquot of the organic phase transferred to a second test tube, and the solution diluted to 10 ml with $CHCl_3$/TEA (1M).

Figure 2:
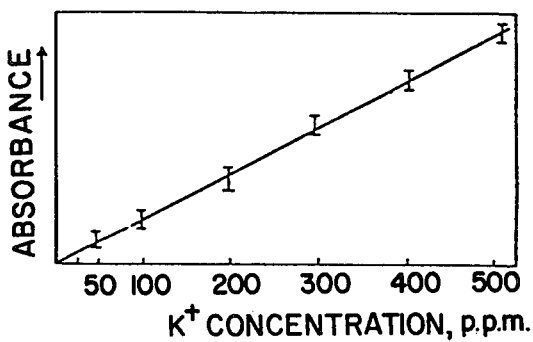
FIG. 2 is a graph showing the increase in absorbance resulting from increases in the level of potassium ion.
Figure 3:
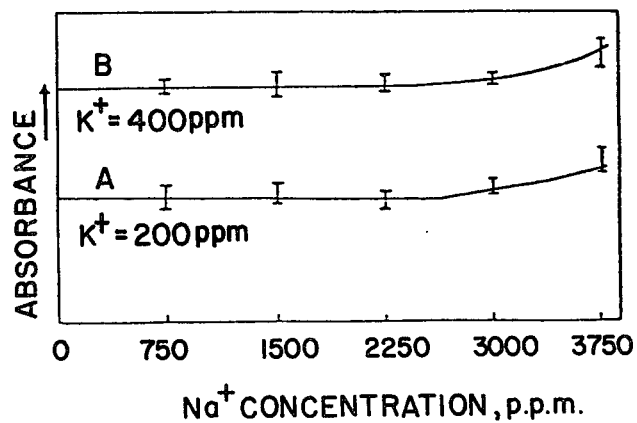
FIG. 3 is a graph showing the effect of sodium ion on the determination of potassium ion at two levels of potassium ion concentration: curve A-200 p.p.m.; curve B-400 p.p.m.

Spectrophotometric measurements were carried out using a Hewlett-Packard 8450 reversed optics spectrophotometer with 10-mm glass cells. The results are summarized in FIG. 2.

EXAMPLE IV

When the procedure of Example III is performed using a solution of 4TF reagent [$2 \times 10^{-3}$ in $CHCl_3$/TEA(1M)] in lieu of 6TF, similar results are obtained.

EXAMPLE V

Determination of extraction constants

In order to determine the extraction constants and the stoicheiometry of the 6TF and 4TF reagent compounds, experiments were run in which the pH and the metal concentration were kept constant while the 6TF and 4TF crown ether concentration in the organic phase was varied. With the exception of the reagent concentration, the extraction procedures and test methods employed were similar to those in Example III.

The test results were analyzed and defined in accordance with prior art procedures. [Takagi, et al., *Anal. Lett.*, 1977, 10, 1115; Nakamura et al., *Talanta*, 1978, 26, 921; Nakamura et al., *Anal. Chem.*, 1980, 52, 1668; Pacey et al., *Anal. Lett.*, 1980, 13, 1085]. Table II shows the data for the extraction constants.

TABLE II

| EXTRACTION CONSTANTS OF 6TF AND 4'-PICRYLAMINOBENZO-15-CROWN-5 A-1 M TEA buffer solution was used. | | |
|---|---|---|
| Ion | 6TF | 4'-Picrylaminobenzyl-15-crown-5 |
| $Na^+$ | NA* | ~10 |
| $K^+$ | 7.5 + 0.2 | 7.5 + 0.2 |
| $Rb^+$ | 8.3 + 0.2 | 8.5 + 0.2 |
| $Ca^+$ | NA | ~10 |

*NA = no appreciable extraction

The data suggests that the sodium and caesium ions will not interfere with the determination of potassium ion using the 6TF reagent, but that the rubidium ion will. However, the rubidium ion has a very low incidence of natural occurance.

EXAMPLE IV

A Determination of potassium ion in blood serum

Four samples of human blood serum were labeled, "A", "B", "C", and "D" and treated as follows.

Each of the serum samples was denatured by admixing 1 ml of the blood serum with 2 ml of 100% ethanol and 2 ml of deionized water. The samples were centrifuged, and the residue discarded.

A solution of $2 \times 10^{-3}$ molar 6TF reagent was prepared by dissolving 1.01 g of 6TF in a liter of organic solvent comprising specroscopic quality chloroform containing freshly distilled triethylamine in the ratio 1 mol TEA per liter $CHCl_3$.

Five milliliters (5 ml) of this 6TF reagent solution was added to each of the aqueous denatured blood serum samples. The samples were shaken for five minutes, the aqueous and non-aqueous phases permitted to separate, and the aqueous phase discarded.

A pipet was utilized to transfer 1 ml aliquots of the organic phases of each of the samples to test tubes. Each 1 ml aliquot was further diluted with 9 ml of chloroform/TEA (1M), and a portion of the dilute sample transferred to a 10 ml glass cell for spectrophotometric measurements. The measurements were carried out at 480 nm using a Hewlett-Packard 8450 A reversed optics spectrophotometer.

The graphic results of the spectrophotometer analysizes were converted to parts per million potassium ion by using the equation:

$$A = (7.62 \pm 0.1) \times 10^{-4} \times [K^+] - (7.04 \pm 3) \times 10^{-4}$$

where A is the absorbance and [K+] is the concentration of potassium ion in parts per million. The results were compared with determination made on the human blood serum samples by means of atomic absorption spectroscopy (AAS). The results are tabulated below:

| | P.P.M. K+ in Blood Serum | |
|---|---|---|
| Sample | 6TF | AAS |
| A | 149 | 155 |
| B | 194 | 196 |
| C | 141 | 150 |
| D | 109 | 115 |

EXAMPLE VII

When the procedure of Example VI is performed using a solution of 4TF reagent in lieu of 6TF reagent, and the absorbance measurements are taken at 585 nm, similar results are obtained.

What is claimed is:

1. Chromogenic crown ethers of the formula

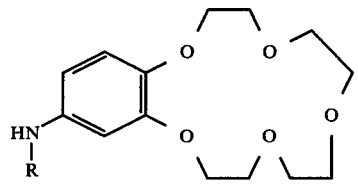

where R is taken from the group consisting of

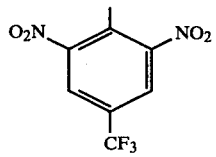 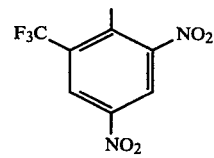

2. 4'-(2'',6''-dinitro-4''-trifluoromethylphenyl) aminobenzo-15-crown-5.

3. 4'-(2'',4''-dinitro-6''-trifluoromethyl-phenyl) aminobenzo-15-crown-5.

4. A process for synthesis of trifluoromethyl-substituted, 15-crown-5 chromogenic ethers, comprising the following steps in sequence:
   (a) forming a reaction mixture in an organic solvent of
      (i) 4'-aminobenzo-15-crown-5,
      (ii) a compound selected from the group consisting of 1-chloro-2,6-dinitro-4-trifluoromethylbenzene, and 1-chloro-2,4-dinitro-6-trifluoromethylbenzene, and
      (iii) a base, and
   (b) isolating a trifluoromethyl-substituted crown ether from said reaction mixture.

* * * * *